US006841557B2

(12) United States Patent
Anderson et al.

(10) Patent No.: US 6,841,557 B2
(45) Date of Patent: Jan. 11, 2005

(54) COMPOUNDS FOR THE TREATMENT OF ADDICTIVE DISORDERS

(75) Inventors: Richard W. Anderson, Annandale, NJ (US); Sylvia S. McBrinn, Stockton, NJ (US); David W. Robertson, Galesburg, MI (US); Robert C. Marshall, Mattawan, MI (US)

(73) Assignee: Pharmacia & Upjohn, Kalamazoo, MI (US)

( * ) Notice: Subject to any disclaimer, the term of this patent is extended or adjusted under 35 U.S.C. 154(b) by 0 days.

(21) Appl. No.: 09/929,666

(22) Filed: Aug. 14, 2001

(65) Prior Publication Data

US 2002/0049206 A1 Apr. 25, 2002

Related U.S. Application Data

(60) Provisional application No. 60/263,610, filed on Jan. 23, 2001, and provisional application No. 60/225,714, filed on Aug. 16, 2000.

(51) Int. Cl.$^7$ ............................................. A61K 31/44
(52) U.S. Cl. ...................... 514/294; 514/292; 514/293; 514/290
(58) Field of Search ................. 514/290, 292, 514/293, 294

(56) References Cited

U.S. PATENT DOCUMENTS

| | | | |
|---|---|---|---|
| 4,526,892 A | 7/1985 | Salvati et al. | 514/288 |
| 5,273,975 A | 12/1993 | Moon et al. | 514/233.2 |
| 5,436,240 A | 7/1995 | Moon et al. | 514/224.5 |
| 5,462,947 A | 10/1995 | Svensson et al. | 514/317 |
| 5,594,024 A | 1/1997 | Svensson et al. | 514/429 |
| 5,877,317 A | 3/1999 | TenBrink et al. | 544/295 |
| 6,008,233 A | 12/1999 | Andino et al. | 514/327 |
| 6,448,258 B2 * | 9/2002 | McCall et al. | 514/292 |
| 6,448,293 B1 * | 9/2002 | Andrews et al. | 514/603 |
| 6,555,548 B2 * | 4/2003 | McCall et al. | 514/288 |

FOREIGN PATENT DOCUMENTS

| | | | |
|---|---|---|---|
| WO | WO 90/15058 | 12/1990 | ......... C07D/455/04 |
| WO | WO 99/10339 | 3/1999 | ......... C07D/401/10 |
| WO | WO 99/24423 | 5/1999 | ......... C07D/401/12 |

OTHER PUBLICATIONS

Caine et al., "$D_3$–receptor test in vitro predicts decreased cocaine self–administreation in rats," *Chem. Abstract* XP002168920, 1997.

Calon et al., "Levadopa or $D_2$ agonist induced dyskinesia in MPTP monkeys: correlation with changes in dopamine and $GABA_A$ receptors in the striatpallidal complex," *Brain Research 680*: 43–52 (1995).

Garner et al., "Analysis of $D_2$ and $D_3$ Receptor–Selective Ligands in Rats Trained to Discriminate Cocaine from Saline," *Pharmacology, Biochemistry and Behavior 64*(2): 373–378 (1999).

Philip L. Gould, "Salt Selection for Basic Drugs, " *International Journal of Pharmaceutics*, 33 (1986) pp. 201–217.

Robert E. Hales, M.D., et al., "Nicotine" section, The American Psychiatric Press Textbook of Psychiatry, Second Edition (1994) pp. 401–402.

Richard I. Shader, Chapter 11 "Hypnosis," Manual of Psychiatric Therapeutics, Second Edition (1994) pp. 81–86.

* cited by examiner

Primary Examiner—Vickie Kim
(74) Attorney, Agent, or Firm—Pharmacia & Upjohn Company; Thomas A. Wootton

(57) ABSTRACT

The treatment of addictive disorders, psychoactive substance use disorders, intoxication disorders, inhalation disorders, alcohol addiction, tobacco addiction, and nicotine addiction using a heterocyclic amine, a phenylazacycloalkane, a cabergoline, or an aromatic bicyclic amine active agent, or a pharmaceutically acceptable derivative or salt of any said active agent is described herein.

12 Claims, No Drawings

COMPOUNDS FOR THE TREATMENT OF ADDICTIVE DISORDERS

This application claims priority from U.S. provisional application Ser. No. 60/263,610 filed on Jan. 23, 2001 and U.S. provisional application Ser. No. 60/225,714 filed on Aug. 16, 2000.

BACKGROUND OF THE INVENTION

1. Field of the Invention

The invention relates to the use of neuromuscular agents, and the pharmacologically acceptable salts thereof, for the treatment of, or improving symptoms of, several nervous system disorders. More particularly, the invention relates to treatment and improvement of symptoms related to addictive disorders, psychoactive substance use disorders, nicotine addiction, and tobacco addiction.

2. Description of Related Technology

Several classes of compounds have been described for the effective treatment and management of the diseases fibromyalgia (FMS) (or fibromyalgia syndrome) and Chronic Fatigue Immune Disorders Syndrome (CFIDS) or Chronic Fatigue Syndrome (CFS). More particularly, heterocyclic amine type compounds, phenylazacycloalkane type compounds, cabergoline and cabergoline-type compounds have been described for the effective treatment and management of these neuromuscular conditions.

Heterocyclic amine compounds and methods of making the same are disclosed in U.S. Pat. No. 5,273,975, issued Dec. 28, 1993; U.S. Pat. No. 5,436,240, issued Jul. 25, 1995; U.S. Pat. No. 5,462,947, issued Oct. 31, 1995; and U.S. Pat. No. 5,594,024, issued Jan. 14, 1997. More particularly, the compounds and the processes for making those compounds, formulations and methods of preparing medicaments are described in U.S. Pat. No. 5,273,975, issued Dec. 28, 1993; and U.S. Pat. No. 5,436,240, issued Jul. 25, 1995, also providing a generic description of compounds having use in the treatment of FMS and CFIDS.

Phenylazacycloalkane compounds and methods of making the same have been described in U.S. Pat. No. 5,594,024, issued Jan. 14, 1997, and U.S. Pat. No. 5,462,947, issued Oct. 31, 1995. The compounds are disclosed as having useful activity in treating central nervous disorders related to dopamine receptor activity.

Cabergoline and cabergoline-type compounds have been disclosed as demonstrating hypotensive and antiprolactinic activity. The compound is commercially available from Pharmacia & UpJohn, Inc. (now Pharmacia Corporation) under the trade names DOSTINEX™ and CABASER™ for hyperprolactinemic disorders and Parkinson's disease. The compounds and methods for making the same are described in U.S. Pat. No. 4,526,892, issued Jul. 2, 1985.

More recently, scientists have considered whether these compounds having useful properties for treating neuromuscular disorders can be used for treating other nervous system disorders, particularly addictive diseases. More particularly, the use of these compounds for nervous systems disorders, for example, addictive disorders, psychoactive substance use disorders, nicotine addiction, or tobacco addiction resulting in smoking cessation, have been considered.

In addition to the previously mentioned compounds, aromatic bicyclic amine compounds have also been investigated for potential activity useful for treating nervous system disorders, such as addictive diseases. The aromatic bicyclic amine compounds have been reported to demonstrate activity useful for treatment of some central nervous system disorders, for example, schizophrenia, and cardiovascular disease, such as cardiac arrhythmias and cardiac fibrillation. Bicyclic amine compounds and methods of making the same are described in U.S. Pat. No. 5,877,317, issued Mar. 2, 1999.

Methods for using the described compounds for treating addictive-type nervous disorders has not been reported. Methods and dosages for using heterocyclic amine compounds, phenylazacycloalkane compounds, cabergoline, aromatic bicyclic amine compounds and the derivatives of these classes of compounds for treating specific addictive disorders are described herein.

SUMMARY OF THE INVENTION

The invention provides a method for the treatment of certain addictive disorders, for example, psychoactive substance use disorders, nicotine addiction or tobacco addiction (with a result of smoking cessation or a decrease in smoking). The method includes the step of administering a therapeutically effective, nontoxic dose of a heterocyclic amine, a phenylazacycloalkane, a cabergoline, or an aromatic bicyclic amine compound, or a pharmaceutically acceptable salt or derivative thereof, to a patient suffering from or susceptible to such an addiction or disorder.

DETAILED DESCRIPTION OF THE INVENTION

Heterocyclic amine, phenylazacycloalkane, cabergoline, aromatic bicyclic amine compounds, and the pharmaceutically acceptable salts or derivatives of these compounds can be used to treat and ameliorate nervous system disorders. The disorders typically can include, but are not limited to, addictive disorders, psychoactive substance use disorders, nicotine addition, tobacco addiction, and other diseases or disorders related to affliction of the nervous system, and more particularly, the central nervous system.

Several compounds demonstrating activity in treating neuromuscular disease have been identified for the method of the invention. The following classes of compounds can be used for treating or suppressing the symptoms of conditions related to nervous system affliction, particularly addictive disorders. Examples of at least the following classes of compounds are provided for the method of the invention.

A suitable compound can have the formula, below:

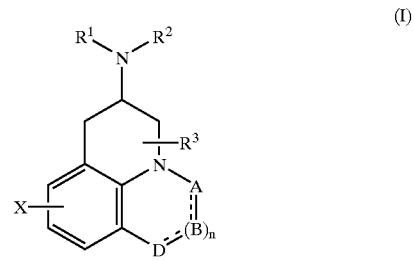

(I)

or a pharmaceutically acceptable salt thereof, wherein:

$R^1$, $R^2$, and $R^3$ are each independently hydrogen, $C_{1-6}$ alkyl, $C_{3-5}$ alkenyl, $C_{3-5}$ alkynyl, $C_{3-7}$ cycloalkyl, $C_{4-10}$ cycloalkyl- or phenyl-substituted $C_{1-6}$ alkyl, or $R^1$ and $R^2$ are joined to form a $C_{3-7}$ cyclic amine which can contain additional heteroatoms and/or unsaturation;

n is 0 or 1;

X is hydrogen, $C_{1-6}$ alkyl, halogen, hydroxy, alkoxy, cyano, carboxamide, carboxyl, or carboalkoxyl;

A is CH, CH$_2$, CH-halogen, CHCH$_3$, C=O, C=S, C—SCH$_3$, C=NH, C—NH$_2$, C—NHCH$_3$, C—NHCOOCH$_3$, C—NHCN, SO$_2$, or N;

B is CH$_2$, CH, CH-halogen, C=O, N, NH, N—CH$_3$, or O; and

D is CH, CH$_2$, CH-halogen, C=O, O, N, NH, or N—CH$_3$.

Preferred compounds of the formula (I) are those wherein D is N or NH, n is 0, and R$^1$, R$^2$, R$^3$, X, A, and B are as previously defined. Additional preferred compounds of formula (I) are those wherein A is CH, CH$_2$, CHCH$_3$, C=O, C=S, C—SCH$_3$, C=NH, C—NH$_2$, C—NHCH$_3$, C—NHCOOCH$_3$, or C—NHCN, and R$^1$, R$^2$, R$^3$, n, X, B, and D are as previously defined.

More preferred compounds of formula (I) for the invention are those wherein A is CH or C=O, and R$^1$, R$^2$, R$^3$, n, X, B, and D are as previously defined.

Compounds of formula (I) can be prepared by any suitable method. The compounds generally can be referred to as heterocyclic amine compounds. Methods for preparing compounds of formula (I) are further described in U.S. Pat. No. 5,273,975, issued Dec. 28, 1993, which is herein incorporated by reference.

Nonlimiting examples of formula (I) for the practice of the invention include, but are not limited to:

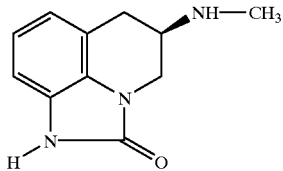

(R)-5,6-dihydro-5-(methylamino)-4H-imadazo[4,5,1-ij]-quinolin-2(1H)-one (uninverted CAS name) or (5R)-5-(methylamino)-5,6-dihydro-4H-imidao[4,5,1-ij]quinolin-(2H)-one (generated by ACD/Name software);

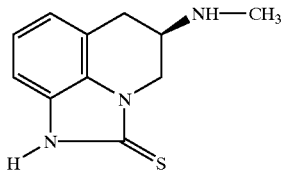

(5R)-5-(methylamino)-5,6-dihydro-4H-imidazo[4,5,1-ij]quinoline-2(1H)-thione; and pharmaceutically acceptable salts thereof.

Pharmaceutically acceptable salts include addition salts of both inorganic and organic acids. The pharmaceutically acceptable salts are preferred over the corresponding free amines since they produce compounds which are more water soluble and more crystalline. The preferred pharmaceutically acceptable salts include salts of the following acids hydrochloric, hydrobromic, sulfuric, phosphoric, nitric, citric, methanesulfonic CH$_3$—(CH$_2$)$_{n1}$—COOH where n1 is 0 thru 4, HOOC—(CH$_2$)$_{n1}$—COOH where n1 is as defined above, and HOOC—CH=CH—COOH. For other pharmaceutically acceptable salts, see *Int. J. Pharm.*, 33, 201–217 (1986).

It is more preferred that the active agent (5R)-5-(methylamino)-5,6-dihydro-4H-imidazo[4,5,1-ij]quinoline-2(1H)-thione be present as the maleate salt, which is (5R)-5-(methylamino)-5,6-dihydro-4H-imidazo[4,5,1-ij]quinoline-2(1H)-thione maleate. A preferred salt of (5R)-5-(methylamino)-5,6-dihydro-4H-imidazo[4,5,1-ij]quinoline-2(1H)-thione is (SR)-5-(methylamino)-5,6-dihydro-4H-imidazo[4,5,1-ij]quinoline-2(1H)-thione 2-butenedicanate.

Other compounds suitable for the invention are those having the formula:

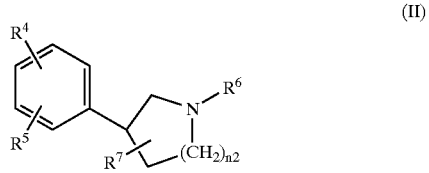

(II)

or a pharmaceutically acceptable salt thereof, wherein:

n2 is 0–3;

R$^4$ and R$^5$ are independently hydrogen, —OH, CN, CH$_2$CN, 2-CF$_3$, 4-CF$_3$, CH$_2$CF$_3$, CH$_2$CHF$_2$, CH=CF$_2$, (CH$_2$)$_2$CF$_3$, ethenyl, 2-propenyl, OSO$_2$CH$_3$, OSO$_2$CF$_3$, SSO$_2$CF$_3$, COR$^7$, COOR$^7$, CON(R$^7$)$_2$, SO$_{x1}$CH$_3$, wherein x1 is 0–2, SO$_{x1}$CF$_3$, O(CH$_2$)$_{x1}$CF$_3$, SO$_2$N(R$^7$)$_2$, CH=NOR$^7$, COCOOR$^7$, COCOON(R$^7$)$_2$, C$_{1-8}$ alkyl, C$_{3-8}$ cycloalkyl, CH$_2$OR$^7$, CH$_2$(R$^7$)$_2$, NR$^7$SO$_2$CF$_3$, NO$_2$, halogen, a phenyl at positions 2, 3 or 4, thienyl, furyl, pyrrole, oxazole, thiazole, N-pyrroline, triazole, tetrazole or pyridine; provided that at least one of R$^4$ and R$^5$ is a substituent other than hydrogen and provided that when R$^4$ or R$^5$ is —OH R$^7$ is other than hydrogen;

R$^6$ is hydrogen, CF$_3$, CH$_2$CF$_3$, C$_1$–C$_8$ alkyl, C$_3$–C$_8$ cycloalkyl, C$_4$–C$_9$ cycloalkyl-methyl, C$_2$–C$_8$ alkenyl, C$_2$–C$_8$ alkynyl, 3,3,3-trifluoropropyl, 4,4,4-trifluorobutyl, —(CH$_2$)$_m$—R$^8$, wherein m is 1–8, CH$_2$SCH$_3$ or a C$_4$–C$_8$ alkyl bonded to said nitrogen and one of its adjacent carbon atoms inclusive to form a heterocyclic structure;

R$^7$ is independently hydrogen, CF$_3$, CH$_2$CF$_3$ C$_1$–C$_8$ alkyl, C$_3$–C$_8$ cycloalkyl, C$_4$–C$_9$ cycloalkyl-methyl, C$_2$–C$_8$ alkenyl, C$_2$–C$_8$ alkynyl, 3,3,3-trifluoropropyl, 4,4,4-trifluorobutyl, —(CH$_2$)$_m$—R$^8$, wherein m is 1–8;

R$^8$ is phenyl optionally substituted with a CN, CF$_3$, CH$_2$CF$_3$, C$_1$–C$_8$ alkyl, C$_3$–C$_8$ cycloalkyl, C$_4$–C$_9$ cycloalkyl-methyl, C$_2$–C$_8$ alkenyl, C$_2$–C$_8$ alkynyl, 2-thiophenyl, 3-thiophenyl, —NR$^9$CONR$^9$R$^{10}$, or —CONR$^9$R$^{10}$; and R$^9$ and R$^{10}$ are each independently hydrogen, C$_1$–C$_8$ alkyl, C$_3$–C$_8$ cycloalkyl, C$_4$–C$_9$ cycloalkylmethyl, C$_2$–C$_8$ alkenyl or C$_2$–C$_8$ alkynyl.

The preferred compounds are at least those compounds of formula (II) wherein:

R$^4$ is CN, and n2, R$^5$, R$^6$, and R$^7$ are as previously defined;

R$^5$ is H, R$^6$ is n-propyl, and n2, R$^4$, and R$^7$ are as previously defined;

R$^4$ is —OSO$_2$CF$_3$, and n2 and R$^5$–R$^7$ are as previously defined;

R$^5$ is H, R$^6$ is C$_{1-8}$ alkyl, and n2, R$^4$, and R$^7$ are as previously defined;

R$^4$ is 3-OH, R$^5$ is H, R$^6$ is n-propyl, R$^7$ is a C$_{1-8}$ alkyl, and n2 is as previously defined;

n2 is 2, and R$^4$–R$^7$ are as previously defined; and n2 is 0, and R$^4$–R$^7$ are as previously defined.

Compounds of formula (II) are described in U.S. Pat. No. 5,594,024, issued Jan. 14, 1997, and U.S. Pat. No. 5,462,947, issued Oct. 31, 1995, each of which is incorporated herein by reference. The compounds can more generally be referred to as phenylazacycloalkane compounds.

Nonlimiting examples of formula (II) for the practice of the invention include, but are not limited to:

(3S)-3-[3-(methylsulfonyl)phenyl]-1-propylpiperidine hydrochloride;

(3S)-3-[3-(methylsulfonyl)phenyl]-1-propylpiperidine hydrobromide; and (3S)-3-[3-methylsulfonyl)phenyl]-1-propylpiperidine (2E)-2-butenedioate.

More compounds suitable for the invention are the active agent cabergoline and derivatives thereof of the formula:

(III)

or a pharmaceutically acceptable salt thereof, wherein:

$R^{11}$ is hydrogen or methyl;

$R^{12}$ is independently hydrogen, halogen, methyl, formyl, S—$R^{17}$, or SO—$R^{17}$, wherein $R^{17}$ is $C_1$–$C_4$ alkyl or phenyl;

$R^{13}$ is hydrogen or methoxy;

$R^{14}$ is independently $C_1$–$C_4$ alkyl, $C_1$–$C_4$ alkenyl, $C_1$–$C_4$ alkynyl, benzyl, or phenyl; and $R^{15}$ and $R^{16}$ are each independently $C_1$–$C_4$ alkyl, cyclohexyl, phenyl optionally substituted with halogen or methoxy, or $(CH_2)_{n3}N(CH_3)_2$, wherein n3 is an integer.

The chemical name for cabergoline is 1-((6-allylergolin-8β-yl)carbonyl)-1-(3-(dimethylamino)propyl)-3-ethylurea. Cabergoline is the generic name for the active ingredient in DOSTINEX™ (Pharmacia & UpJohn, Inc., Kalamazoo, Mich., now Pharmacia Corporation), which is sold in the United States as a treatment for hyperprolactinemic disorders, and CABASER™ (Pharmacia & UpJohn, Inc.), which is sold in Europe as a treatment for Parkinson's disease. The synthesis and use of cabergoline and some useful derivatives thereof are disclosed and claimed in U.S. Pat. No. 4,526,892, which is incorporated herein by reference. More specifically, the compounds disclosed generically and specifically in claims 1–4 of U.S. Pat. No. 4,526,892 are incorporated herein by reference.

Another class of compounds suitable for the invention is the aromatic bicyclic amine compounds of the formula:

(IV)

wherein:

n3 is 0 or 1;

n4 is 0 or 1, provided that $R^{20}$ is not present when n4 is 0;

$R^{18}$ (1) is α-$R^{18-1}$:β-$R^{18-2}$ where one of $R^{18-1}$ or $R^{18-2}$ is selected from the group consisting of H or $C_1$–$C_6$alkyl, and the other of $R^{18-1}$ or $R^{18-2}$ is a group of the formula:

wherein $R^{26}$ and $R^{27}$ are independently selected from H or $C_1$–$C_6$-alkyl; $R^{28}$ is oxygen (O) or $R^{28}$ is α-$R^{28-1}$:β-$R^{28-2}$, wherein $R^{28-1}$ and $R^{28-2}$ are independently selected from H or $C_1$–$C_6$ alkyl; $R^{29}$ is selected from the group consisting of wherein $R^{31}$ and $R^{33}$ are independently selected from H or $C_1$–$C_6$ alkyl; $R^{32}$ is nitrogen (N—) or methine (HC—); and s is 1 or 2;

wherein $R^{34}$ is selected from the group consisting of H, $C_1$–$C_6$ alkyl, $C_3$–$C_7$ cycloalkyl, —$C_1$–$C_3$ alkyl-($C_3$–$C_7$ cycloalkyl); and S2 is 0, 1, or 2;

wherein $R^{34}$ and s2 are as defined above;

$R^{19}$ is oxygen (O) or sulfur (S);

$R^{20}$ is α-$R^{20-1}$: β-$R^{20-1}$, wherein one of $R^{20-1}$ and $R^{20-2}$ is H, $C_1$–$C_6$ alkyl, and the other of $R^{20-1}$ or $R^{20-2}$ is H, $C_1$–$C_6$ alkyl, phenyl, hydroxy, and —O—($C_1$–$C_3$ alkyl);

$R^{21}$ is α-$R^{21-1}$: β-$R^{21-2}$, wherein one of $R^{21-1}$ and $R^{21-2}$ is H, $C_1$–$C_6$ alkyl, and the other of $R^{21-1}$ or $R^{21-2}$ is H, $C_1$–$C_6$ alkyl, phenyl, hydroxy, and —O—($C_1$–$C_3$ alkyl);

and when n4 is 1, one of $R^{20-1}$ or $R^{20-2}$ and one of $R^{21-1}$ or $R^{21-2}$ can be taken together with the carbon atoms to which they are attached to form a carbon ring of 5-, 6-, or 7-members;

$R^{22}$ is H, F, Cl, Br, I, —$CONR^{35}R^{36}$, —$SONR^{35}R^{36}$, $CF_3$, $NR^{35}R^{36}$, $NO_2$, CN, —$NR^{35}$—CO—$R^{36}$—$SO_2CF_3$, $C_1$–$C_4$ alkyl, $Si(CH_3)_3$, and phenyl optionally substituted with one or two substituents selected from the group consisting of F, Cl, Br, I, and —CO—$NR^{35}R^{36}$, wherein $R^{35}$ and $R^{36}$ are independently selected from the group consisting of H, $C_1$–$C_6$ alkyl, $C_3$–$C_7$ cycloalkyl, and —$C_1$–$C_3$ alkyl-($C_3$–$C_7$ cycloalkyl);

and where $R^{22}$ and one of $R^{21-1}$ or $R^{21-2}$ are taken together with the carbon atoms to which they are attached to form a carbon ring of 5-, 6-, or 7-members;

$R^{23}$ is H, F, Cl, Br, I, —$CONR^{37}R^{38}$, —$SONR^{37}R^{38}$, $CF_3$, $NR^{37}R^{38}$, $NO_2$, CN, —$NR^{37}$—CO—$R^{38}$, —$SO_2CF_3$, $C_1$–$C_4$ alkyl, $Si(CH_3)_3$, and phenyl optionally substituted with one or two substituents selected from the group consisting of F, Cl, Br, I, and —CO—$NR^{37}R^{38}$, wherein $R^{37}$ and $R^{38}$ are independently selected from the group consisting of H, $C_1$–$C_6$ alkyl, $C_3$–$C_7$ cycloalkyl, and —$C_1$–$C_3$ alkyl-($C_3$–$C_7$ cycloalkyl);

$R^{24}$ is H, F, Cl, Br, I, —$CONR^{39}R^{40}$, —$SONR^{39}R^{40}$, $CF_3$, $NR^{39}R^{40}$, $NO_2$, CN, —$NR^{39}$—CO—$R^{40}$, —$SO_2CF_3$, $C_1$–$C_4$ alkyl, $Si(CH_3)_3$, and phenyl optionally substituted with one or two substituents selected from the group consisting of F, Cl, Br, I, and —CO—$NR^{39}R^{40}$, wherein $R^{39}$ and $R^{40}$ are independently selected from the group consisting of H, $C_1$–$C_6$ alkyl, $C_3$–$C_7$ cycloalkyl, and —$C_1$–$C_3$ alkyl-($C_3$–$C_7$ cycloalkyl);

$R^{25}$ is H, F, Cl, Br, I, —CONR $R^{41}R^{42}$, —$SONR^{39}R^{40}$, $CF_3$, $NR^{41}R^{42}$, $NO_2$, CN, —$NR^{41}$—CO—$R^{42}$, —$SO_2CF_3$, $C_1$–$C_4$ alkyl, $Si(CH_3)_3$, and phenyl optionally substituted with one or two substituents selected from the group consisting of F, Cl, Br, I, and —CO—$NR^{41}R^{42}$, wherein $R^{41}$ and $R^{42}$ are independently selected from the group consisting of H, $C_1$–$C_6$ alkyl, $C_3$–$C_7$ cycloalkyl, and —$C_1$–$C_3$ alkyl-($C_3$–$C_7$ cycloalkyl);

with the proviso that not more than two of $R^{22}$, $R^{23}$, $R^{24}$, and $R^{25}$ are other than H; and $R^{30}$ is selected from the group consisting of:
phenyl optionally substituted with one or two substituents selected from the group consisting of $CF_3$, $COR^{43}$, $COOR^{43}$, CN, $NO_2$, $NR^{44}$—CO—$R^{45}$, —S—($C_1$–$C_6$ alkyl), $NR^{44}R^{45}$, or a group represented by $R^{46}$;

2-, 3-, and 4-pyridinyl optionally substituted with one or two substituents represented by $R^{46}$; and 2-, 4-, and 5-pyrimidinyl optionally substituted with one or two substituents represented by $R^{46}$;

wherein $R^{43}$, $R^{44}$ and $R^{45}$ are independently selected from the group consisting of H, $C_1$–$C_6$ alkyl, $C_3$–$C_7$ cycloalkyl, —$C_1$–$C_3$ alkyl-($C_3$–$C_7$ cycloalkyl); and $R^{46}$ is selected from the group consisting of F, Cl, Br, I, —CO—$NR^{44}R^{45}{}_1$, —$SO_2NR^{44}R^{45}$, OH, SH, $C_1$–$C_6$ alkyl, $C_3$–$C_6$ cycloalkyl, —$OR^{47}$, —$CH_2$-($C_3$–$C_6$ cycloalkyl), —$CH_2$-phenyl, $C_3$–$C_6$ cycloalkyl, —$SO_2CF_3$, and —$CH_2CF_3$, wherein $R^{44}$ and $R^{45}$ are as previously defined and $R^{47}$ is $C_1$–$C_6$ alkyl;

and enantiomers and diasteromers thereof, where such exist, and pharmaceutically acceptable salts thereof.

Compounds of formula (IV) are described in U.S. Pat. No. 5,877,317, issued Mar. 2, 1999, which is herein incorporated by reference. Aromatic bicyclic amine compounds, as well as methods for making and using the compounds, are disclosed in U.S. Pat. No. 5,877,317. More particularly, aromatic bicyclic amine compounds are claimed in claims 1–18 of U.S. Pat. No. 5,877,317.

Preferred compounds of formula (IV) are those wherein one of the substituents represented by $R^{18-1}$ or $R^{18-2}$ is H, and the other substituent represented by $R^{18-1}$ or $R^{18-2}$ is a group of the formula:

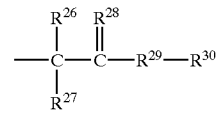

wherein $R^{26}$, $R^{27}$, $R^{28}$, $R^{29}$ and $R^{30}$ are as previously defined.

Nonlimiting examples of formula (IV) for the practice of the invention include, but are not limited to, compounds selected from the group consisting of:
1-(4-fluorophenyl)-4-[2-(isochroman-1-yl)ethyl] piperazine,
1-[2-(isochroman-1-yl)ethyl]-4-phenylpiperazine,
1-[2-(isochroman-1-yl)ethyl]-4-(4-methoxyphenyl) piperazine,
(–)-4-[4-[2-(isochroman-1-yl)ethyl]piperazin-1-yl] benzamide, and
(–)-4-[4-[2-(isochroman-1-yl)ethyl]piperazin-1-yl] benzenesulfonamide.

The preferred compound is (–)-4-[4-[2-(isochroman-1-yl) ethyl]piperazin-1-yl]benzenesulfonamide, or (–)-4-[4-[2-(3, 4-dihydro-1H-2-benzopyran-1-yl)ethyl]-1-piperazinyl]-benzenesulfonamide, or 4-(4-(2-[(1S)-3,4-dihydro-1H-isochromen-1-yl]ethyl)-1-piperazinyl)benzenesulfonamide (Generated by ACD/Name software).

The term "alkyl" as used herein refers to The notation "$C_y$–$C_z$" denotes a hydrocarbon chain containing from y carbon atoms to z carbon atoms. For example, the term $C_1$–$C_6$ alkyl refers to a straight or branched alkyl group of from about 1 to about 6 carbon atoms, such as methyl, ethyl, n-propyl, iso-propyl, n-butyl, iso-butyl, sec-butyl, tert-butyl, n-pentyl, neo-pentyl, n-hexyl, iso-hexyl, and the like.

As used herein, the term "alkenyl" refers to a radical of an aliphatic, unsaturated hydrocarbon containing at least one double bond, including branched and unbranched forms. Examples of alkenyl groups include, but are not limited to, ethenyl, 1-methyl-1-ethenyl, 1-propenyl, 2-propenyl, 1-butenyl, 2-butenyl, 3butenyl, 2-methyl-1-butenyl, 1-pentenyl, 2-pentenyl, 3-pentenyl, 4-pentenyl, 1-methyl-4-pentenyl, 3-methyl-1-pentenyl, 3-methyl,-2-pentenyl, 1-hexenyl, 2-hexenyl, 3-hexenyl, and the like.

The term "alkynyl" as used herein refers to an aliphatic unsaturated hydrocarbon containing at least one triple bond, including branched and unbranched forms. Examples of alkynyl groups are 1-propynyl, 2-propynyl, 1-butynyl, 2-butynyl, 3-butynyl, 2-methyl-1-butynyl, 1-pentynyl, 2-pentynyl, 3-pentynyl, 4-pentynyl, 1-methyl-4-pentynyl, 3-methyl-1-pentynyl, 3-methyl, 2-pentynyl, 1-hexynyl, 2-hexynyl, 3-hexynyl, and the like.

The term "cycloalkyl" as used herein refers to non-aromatic cyclic hydrocarbon group, preferably containing from three to six carbon atoms. Examples of cycloalkyl are cyclopropyl, cyclobutyl, cyclopentyl, cyclohexyl, and the like. Cycloalkyl groups also can have alkyl and alkoxy groups, as defined above, as well as halo substituents, for example, bromo, chloro, iodo, and fluoro.

The term "cycloalkyl-substituted alkyl" as used herein refers to an alkyl group as defined above, wherein at least one carbon atom of the alkyl group is attached to a cycloalkyl group as defined above.

As used herein, the term "phenyl-substituted alkyl" as used herein refers to an alkyl group as defined above, wherein at least one carbon atom of the alkyl group is attached to a phenyl group, i.e. a substituted or unsubstituted radical derivatized from benzene comprising a 6-membered aromatic ring.

The term "halogen" as used herein refers to the typical halogen atoms, for example, bromine, chlorine, iodine, and fluorine.

The term "hydroxy" refers to the group —OH.

The term "alkoxy" as used herein refers to a straight or branched hydrocarbon group as defined above attached to the parent molecule through an oxygen heteroatom, typically by a carbon to oxygen bond. The hydrocarbon of the alkoxy group preferably contains from 1 to 6 carbon atoms. Typical alkoxy groups are methoxy, ethoxy, n-propoxy, isopropoxy, n-butoxy, sec-butoxy (1-methylpropoxy), t-butoxy (1,1-dimethylethoxy), n-pentoxy, t-pentoxy (1,1-dimethylpropoxy), and the like.

The term "aryl" as used herein refers to an aromatic cyclic hydrocarbon, such as phenyl and naphthyl. The aryl group, such as phenyl groups, optionally can be substituted with alkyl, alkoxy or a halo group, for example, bromo, chloro, iodo, and fluoro. Examples of aryl groups include, but are not limited to, phenyl, bromophenyl, chlorophenyl, iodophenyl, fluorophenyl, bromonaphthyl, and the like.

The term "cyano" as used herein refers to the group —CN.

The term "carboxamide" as used herein refers to the group —CONH$_2$.

The term "carboxyl" as used herein refers to the group —COOH.

The term "carboalkoxyl" as used herein refers to a group —COOR wherein R is ower alkyl, such as carboxymethoxy, carboethoxy, and the like.

The term "thienyl" as used herein refers to the radical derived from thiophene.

The term "furyl" as used herein refers to the radical derived from furan, and its derivatives, including tetrahydrofuran, e.g. tetrahydrofuryl.

The term "pyrrole" as used herein refers to all isomers of the pyrrole ring, including 2H-pyrrole, pyrrole, 2-pyrroline, and like.

The term "cycloalkylmethyl" as used herein refers to a cycloalkyl group attached to the parent compound by a methylene (—CH$_2$—) group.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. More particularly, the term "pharmaceutically acceptable salts" as used herein refers to organic and inorganic acid addition salts of the parent compound.

The dosages to be given with the compounds above can be easily determined by a skilled physician with experience in prescribing biologically active drugs designed to modulate central nervous system, movement and related psychological and physiological disorders, preferably of the disorders described herein. While the active agent generally is administered once a day or twice a day, it can be administered more, or less, frequently, as is suitable, and in the dosages desired for the particular patient.

Any conventional pharmaceutical preparations can be used, e.g., consisting essentially of an inert pharmaceutical carrier and an effective dose of the active substance; e.g., plain or coated tablets, capsules, lozenges, powders, solutions, suspensions, emulsions, syrups, suppositories, transdermal patch, and other useful mediums for delivering the active agent. Preferably, the active agent is formulated into oral dose tablets.

Preferred oral dose tablets comprise the active agent and a pharmaceutically acceptable carrier. The preferred pharmaceutically acceptable carrier can comprise one or more inert excipients, for example, mannitol, maize starch, colloidal silica, povidone, and magnesium stearate.

Tablets containing heterocyclic amine compounds, phenylazacycloalkane compounds, and cabergoline or cabergoline-type compounds typically incorporate, in mg/tablet, the following amounts of active agent: 0.125, 0.25, 0.5, 1.0, 1.25 and 1.5 mg. The preferred starting dose for the administration of these compounds is about 0.125 mg/day, provided to a patient three times per day (tid). The dose may be increased from the initial dosage to a higher amount with increases every five to seven days up to a maximum dose of 10 mg/day. A preferred higher total daily dosage is about 6 mg/day. A more preferred higher dosage is about 4.5 mg/day to 5 mg/day.

Dosages of the aromatic bicyclic amine compounds can be from about 5 mg of the aromatic bicyclic amine active agent to about 120 mg of the aromatic bicyclic amine active agent per day. Preferably, an aromatic bicyclic amine active agent is administered in an amount of about 20 mg/day to about 100 mg/day. More preferably, an aromatic bicyclic amine active agent is administered in an amount of about 40 mg/day to about 80 mg/day. The aromatic bicyclic amine compounds, like other compounds suitable for the invention, can be administered at an initial dose strength that is later increased to a suitable maximum daily dose.

For treating the addictive disorders described herein the drug may also be provided in chewable format, such as a chewing gum. The amount of active drug included in a chewable base may be half the dosage suggested above for the tablet, for example starting with about 0.075 mg of cabergoline per square of chewing gum being administered tid and followed with higher levels after the patient shows tolerance to the drug. Chewing gum dosages contemplated within the scope of the invention include at least 0.075, 0.10, 0.125, 0.150 mg/day, in addition to those mentioned for a tablet for heterocyclic amine compounds, phenylazacycloalkane compounds, and cabergoline or cabergoline-type compounds. Similarly, dosages contemplated for the aromatic bicyclic amine compounds include from about 2.5 mg/day to about 125 mg/day. One or two chewing gum squares can be provided to the patient up to three times a day, depending on the therapeutic need of the recipient.

Transdermal administration, such as with a skin patch application, and inhalation therapy, such as with an inhaler, also are foreseen where the patch or inhaler would deliver desired levels of the active agent to the patient. A transdermal patch containing the active agent also could be combined with a patch containing nicotine to eliminate a patient's craving for tobacco-containing products.

The drug first is typically administered to a patient at a low dosage to avoid possible nausea that may occur with higher starting doses. The dose is then titrated up to higher levels until a suitable therapeutic effect is achieved.

The effective dose range can be from 0.01 mg/day to about 10.0 mg/day per patient for a heterocyclic amine, phenylazacycloalkane, cabergoline, or cabergoline-type derivative. The preferred effective dose is an amount of the active agent between about 0.125 mg/day and about 6 mg/day. The more preferred effective dose is an amount of the active agent between about 0.375 mg/day to about 5 mg/day. An especially preferred effective dose is an amount of the active agent between about 0.75 mg/day and 4.5 mg/day to a patient. In addition to being administered by oral or intravenous route, the active agent also can be administered transdermally or by inhalation.

In the practice of the invention, typically a starting dose of about 0.125 mg/day, administered three times per day, is incrementally increased every five to seven days until optimal therapeutic effect is achieved. The dosage can be titrated to achieve a maximal therapeutic effect, provided that the patient does not experience intolerable side effects. One ordinarily skilled in art of providing medicine, such as a physician or pharmacist can determine the optimal dosage level after considering a patient's age, size, medical history, responsiveness to and toleration for the drug.

Addictive disorders and psychoactive substance use disorders, such as intoxication disorders, inhalation disorders, alcohol addiction, tobacco addiction and/or nicotine addiction can be treated according to the invention. Tobacco and nicotine addiction would be treated with the goal of achieving either smoking cessation or at least a reduction in the intake of tobacco and/or nicotine. General descriptions of addictive disorders, including disorders related to intoxication, inhalants, and tobacco addiction or nicotine addiction can be found in many standard sources. The addictions and behaviors that can be treated by the invention generally are further described in, for example, *The American Psychiatric Press Textbook of Psychiatry, Second Edition*, edited by Robert E. Hales, Stuart C. Yudofsky, and John A. Talbott, 1994, incorporated by reference, especially pp. 401 et. seq., section on "Nicotine" incorporated by reference; and *Manual of Psychiatric Therapeutics, Second Edition*, edited by Richard I. Shader, incorporated by reference, especially pp. 85 from Chapter 11, entitled "Hypnosis".

The method is particularly useful for the treatment of and relief from alcohol and other psychoactive substance use disorders such as, for example, disorders related to intoxication or inhalants, more particularly tobacco or nicotine addiction. The effect of the invention on tobacco addiction more particularly involves the administration of the active agent in a manner and form that reduces the symptoms of the disease. In particular, the tobacco- and/or nicotine-related aspect of the invention can be used to reduce or stop the smoking or chewing of nicotine-containing materials by a patient.

Without further elaboration, it is believed that one skilled in the art can, using the preceding description, practice the invention to its fullest extent. Those skilled in the art will promptly recognize appropriate variations from the procedures both as to reactants and as to reaction conditions and techniques.

What is claimed is:

1. A method of treating or suppressing the symptoms of addictive disorders selected from the group consisting of alcohol addiction, tobacco addiction, nicotine addiction, and intoxication and inhalation disorders associated with alcohol, tobacco and nicotine addiction, said method comprising the step of administering to a patient in need of treatment a therapeutically effective, nontoxic amount of an active agent wherein the active agent is a heterocyclic amine of the formula:

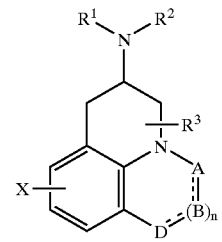

or a pharmaceutically acceptable salt thereof, wherein:
$R^1$, $R^2$, and $R^3$ are each independently hydrogen, $C_{1-6}$ alkyl, $C_{3-5}$ alkenyl, $C_{3-5}$ alkynyl, $C_{3-7}$ cycloalkyl, $C_{4-10}$ cycloalkyl- or phenyl-substituted $C_{1-6}$ alkyl, or $R^1$ and $R^2$ are joined to form a $C_{3-7}$ cyclic amine which can contain additional heteroatoms and/or unsaturation;
n is 0 or 1;
X is hydrogen, $C_{1-6}$ alkyl, halogen, hydroxy, alkoxy, cyano, carboxamide, carboxyl, or carboalkoxyl;
A is CH, $CH_2$, CH-halogen, $CHCH_3$, C=O, C—S, C—$SCH_3$, C=NH, C—$NH_2$, C—$NHCH_3$, C—$NHCOOCH_3$, C—NHCN, $SO_2$, or N;
B is $CH_2$, CH, CH-halogen, C=O, N, NH, N—$CH_3$, or O; and
D is $CH_2$, CH, CH-halogen, C=O, O, N, NH, or N—$CH_3$.
and pharmaceutically acceptable derivatives or salts of said active agent.

2. The method of claim 1, wherein:
D is N or NH, n is 0; or
A is CH, $CH_2$, $CHCH_3$, C=O, C=S, C—$SCH_3$, C=NH, C—$NH_2$, C—$NHCH_3$, C—NHCOOCH—, or C—NHCN.

3. The method of claim 1 wherein the active agent is selected from the group consisting of:
(5R)-5-(methylamino)-5,6-dihydro-4H-imidazo[4,5,1-ij]quinolin-2(1H)-one;
(5R)-5-(methylamino)-5,6-dihydro-4H-imidazo[4,5,1-ij]quinoline-2(1H)-thione;
(5R)-5-(methylamino)-5,6-dihydro-4H-imidazo[4,5,1-ij]quinoline-2(1H)-thione maleate; and
(5R)-5-(methylamino)-5,6-dihydro-4H-imidazo[4,5,1-ij]quinoline-2(1H)-thione 2-butenedioanate.

4. The method of claim 1 wherein the active agent is used to treat or enhance the treatment of tobacco and/or nicotine addiction.

5. The method of claim 1 wherein the active agent is used to reduce the craving for tobacco and/or nicotine containing products.

6. The method of claim 1 wherein the active agent is used to reduce the smoking and/or chewing of tobacco or nicotine-containing products.

7. The method of claim 1 wherein the active agent is administered to the patient three times a day.

8. The method of claim 1 wherein the active agent is administered in a dose of about 0.01 mg/day to about 10.0 mg/day.

9. The method of claim 8 wherein the active agent is administered in a dose of about 0.125 mg/day to about 6 mg/day.

10. The method of claim 9 wherein the active agent is administered in an amount from about 0.375 mg/day to about 5 mg/day.

11. The method of claim 10 wherein the active agent is administered in an amount from about 0.75 mg/day to about 4.5 mg/day.

12. The method of claim 8 wherein an initial dose of active agent of about 0.125 mg/day administered to the patient three times a day is titrated to higher levels every five to seven days until therapeutic effect is achieved.

* * * * *

UNITED STATES PATENT AND TRADEMARK OFFICE
CERTIFICATE OF CORRECTION

PATENT NO. : 6,841,557 B2
DATED : January 11, 2005
INVENTOR(S) : Richard W. Anderson et al.

It is certified that error appears in the above-identified patent and that said Letters Patent is hereby corrected as shown below:

<u>Column 12,</u>
Line 26, delete "C—S," and insert -- C=S, --.
Line 30, delete "O; and" and insert -- O; --.
Line 36, delete "NH, n" and insert -- NH, and n --.
Line 38, delete "C—NHCOOCH—," and insert -- C-NHCOOCH$_3$, --.

Signed and Sealed this

Second Day of May, 2006

JON W. DUDAS
*Director of the United States Patent and Trademark Office*